United States Patent [19]

Sutherland et al.

[11] Patent Number: 4,996,228

[45] Date of Patent: * Feb. 26, 1991

[54] MACROLIDE ANTIBIOTICS

[75] Inventors: Derek R. Sutherland, Chalfont St Giles; Michael V. J. Ramsay, South Harrow; John B. Ward, Bushey; Neil Porter, Pinner; Hazel M. Noble, Burnham; Richard A. Fletton, Ruislip; David Noble, Burnham, all of England

[73] Assignee: American Cyanamid Company, Stamford, Conn.

[ * ] Notice: The portion of the term of this patent subsequent to Dec. 18, 2007 has been disclaimed.

[21] Appl. No.: 24,681

[22] Filed: Mar. 11, 1987

[30] Foreign Application Priority Data

Mar. 12, 1986 [GB] United Kingdom ............... 8606105

[51] Int. Cl.$^5$ .................. A61K 31/335; C07D 313/00
[52] U.S. Cl. .................................... 514/450; 549/264
[58] Field of Search ................... 549/264; 514/450

[56] References Cited

U.S. PATENT DOCUMENTS 4,259,240  3/1981  Wiesner et al. ............... 540/94
4,576,931  3/1986  Umezawa et al. ............... 536/7.1

FOREIGN PATENT DOCUMENTS 0170006  2/1986  European Pat. Off. .

Primary Examiner—Glennon H. Hollrah
Assistant Examiner—Amelia A. Owens
Attorney, Agent, or Firm—Bacon & Thomas

[57] ABSTRACT

Compounds are described of formula (I)

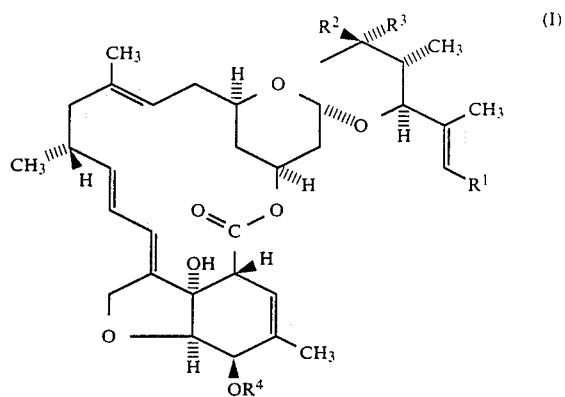

and salts therof, wherein $R^1$ represents a methyl, ethyl or isopropyl group;
$R^2$ is alkyl; alkyl substituted by a carboxy or alkoxycarbonyl; alkenyl; phenyl or phenalkyl;
$R^3$ is —OH;
$OR^4$ is a hydroxyl group or a substituted hydroxyl group having up to 25 carbon atoms.

These compounds may be used for controlling insect, acarine, nematode or other pests.

8 Claims, No Drawings

MACROLIDE ANTIBIOTICS

This invention relates to novel antibiotic compounds and to processes for their preparation.

In our United Kingdom Patent Specification No. 2166436A we describe the production of Antibiotics S541 which may be isolated from the fermentation products of a novel Streptomyces sp.

We have now found a further group of compounds with antibiotic activity which may be prepared by chemical modification of Antibiotics S541. The novel compounds of the invention have antibiotic activity and/or are of use as intermediates in the preparation of other active compounds.

Thus, the present invention provides the compounds of formula (I):

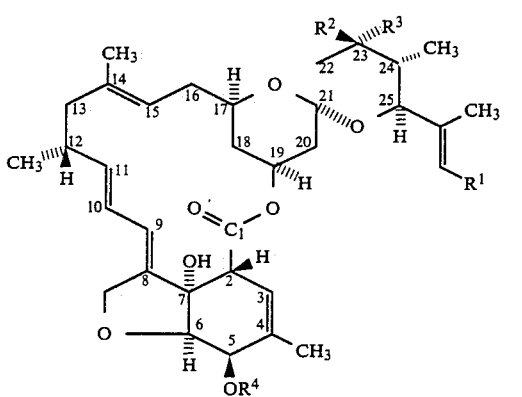

and salts thereof, wherein
$R^1$ is a methyl, ethyl or isopropyl group;
$R^2$ is a $C_{1-4}$ alkyl group [optionally substituted by a group $CO_2R^5$ (where $R^5$ is a hydrogen atom or a $C_{1-4}$ alkyl group)], a $C_{2-6}$ alkenyl group, phenyl or phenyl $C_{1-3}$ alkyl group;
$R^3$ is a hydroxy group; and
$OR^4$ is a hydroxyl or substituted hydroxyl group having up to 25 carbon atoms.

The compounds of formula (I) are of use as antibiotics and/or as intermediates in the preparation of further active compounds.

Salts which may be formed with acidic compounds of formula (I) include alkali metal salts such as sodium and potassium salts.

When the compounds of formula (I) are to be used as intermediates, the group $-OR^4$ will often be a protected hydroxy group and the invention particularly includes such protected compounds.

In general, when the group $R^2$ is a $C_{1-4}$ alkyl group it may be for example a methyl, ethyl, propyl or butyl group.

When $R^2$ is a $C_{2-6}$ alkenyl group it may be for example a vinyl or allyl group.

In general, the group $R^4$ may represent an acyl group e.g. a group of the formula $R^7CO-$ or $R^7OCO-$ or $R^7OCS-$ (where $R^7$ is an aliphatic, araliphatic or aromatic group, for example an alkyl, alkenyl, alkynyl, cycloalkyl, aralkyl or aryl group), a formyl group, a group $R^8$ which is as defined above for $R^7$, a group $R^9SO_2-$ (where $R^9$ is a $C_{1-4}$ alkyl or $C_{6-10}$ aryl group), a silyl group, cyclic or acyclic acetal group, a group $R^{10}OCO(CH_2)_nCO-$ (where $R^{10}$ is a hydrogen atom or a group as defined for $R^7$ above and n represents zero, 1 or 2) or a group $R^{11}R^{12}NCO$ (where $R^{11}$ and $R^{12}$ may each independently represent a hydrogen atom or a $C_{1-4}$ alkyl group e.g. methyl).

Where $R^7$ or $R^8$ are alkyl groups, they may be for example $C_{1-8}$ alkyl groups, e.g. methyl, ethyl, n-propyl, i-propyl, n-butyl, i-butyl, t-butyl or n-heptyl which alkyl groups may also be substituted. Where $R^7$ is a substituted alkyl group it may be substituted by, for example, one or more, e.g. two or three, halogen atoms (e.g. chlorine or bromine atoms), or a carboxy, $C_{1-4}$ alkoxy (e.g. methoxy, ethoxy), phenoxy or silyloxy group. Where $R^8$ is a substituted alkyl group it may be substituted by a cycloalkyl e.g. cyclopropyl group.

Where $R^7$ and $R^8$ are alkenyl or alkynyl groups, they preferably have 2-8 carbon atoms and where they are cycloalkyl groups, they may be for example $C_{3-12}$ cycloalkyl, such as $C_{3-7}$ cycloalkyl, e.g. cyclopentyl groups.

Where $R^7$ and $R^8$ are aralkyl groups, they preferably have 1-6 carbon atoms in the alkyl moiety, and the aryl group(s) may be carbocyclic or heterocyclic and preferably contain 4-15 carbon atoms e.g. phenyl. Examples of such groups include phen $C_{1-6}$ alkyl, e.g. benzyl groups.

Where $R^7$ and $R^8$ are aryl groups, they may be carbocyclic or heterocyclic and preferably have 4-15 carbon atoms e.g. phenyl.

When $R^4$ is a group $R^9SO_2-$, it may be for example a methylsulphonyl or p-toluenesulphonyl group.

Where $R^4$ represents a cyclic acetal group, it may for example have 5-7 ring members as in the tetrahydropyranyl group.

When $R^4$ represents a silyl group or $R^7$ contains a silyloxy substituent, the silyl group may carry three groups which may be the same or different, selected from alkyl, alkenyl, alkoxy, cycloalkyl, aralkyl, aryl and aryloxy groups. Such groups may be as defined above and particularly include methyl, t-butyl and phenyl groups. Particular examples of such silyl groups are trimethylsilyl and t-butyldimethylsilyl.

Where $R^4$ represents a group $R^{10}OCO(CH_2)_nCO-$, it may for example be a group $R^{10}OCOCO-$ or $R^{10}OCOCH_2CH_2CO-$ where $R^{10}$ represents a hydrogen atom or a $C_{1-4}$ alkyl (e.g. methyl or ethyl) group.

In the compounds of formula (I), the group $R^1$ is preferably an isopropyl group.

The group $OR^4$ in the compounds of formula (I) is preferably a methoxycarbonyoxy group or more preferably an acetoxy, methoxy or hydroxy group. In general, compounds of formula (I) in which $OR^4$ is a hydroxy group are particularly preferred.

Important compounds of formula (I) include those in which $R^1$ is an isopropyl group, $R^2$ is a vinyl or allyl group or more preferably a methyl or ethyl group, $R^3$ is a hydroxy group and $-OR^4$ is a hydroxy, methoxy or acetoxy group.

As indicated previously, the compounds according to the invention may be of use as antibiotics and/or as intermediates for the preparation of further active compounds. When the compounds of the invention are to be used as intermediates, the $R^4$ group will serve as a protecting group. It will be appreciated that such a protecting group should have the minimum of additional functionality to avoid further sites of reaction and should be selectively removable. Examples of groups serving as hydroxyl protecting groups are well known and are described, for example, in "Protective Groups in Organic Synthesis" by Theodora W. Greene. (Wiley-Interscience, New York 1981) and "Protective Groups in Organic Chemistry" by J. F. W. McOmie (Plenum Press, London, 1973). Examples of suitable $R^4$ protecting groups include phenoxyacetyl, silyloxyacetyl, (e.g. trimethylsilyloxyacetyl and t-butyldimethylsilyloxyacetyl), and silyl such as trimethylsilyl and t-butyldimethylsilyl. Compounds of the invention containing such groups will primarily be of use as intermediates. Other groups, such as acetyl, may serve as protecting groups, but may also be present in final active compounds.

Compounds of the invention have antibiotic activity e.g. antihelminthic activity, for example against nematodes, and in particular, anti-endoparasitic and anti-ectoparasitic activity.

The compounds of the invention are therefore of use in treating animals and humans with endoparasitic and/or ectoparasitic infections.

Ectoparasites and endoparasites infect humans and a variety of animals and are particularly prevalent in farm animals such as pigs, sheep, cattle, goats and poultry (e.g. chickens and turkeys), horses, rabbits, game-birds, caged birds, and domestic animals such as dogs, cats, guinea pigs, gerbils and hamsters. Parasitic infection of livestock, leading to anaemia, malnutrition and weight loss is a major cause of economic loss throughout the world.

Examples of genera of endoparasites infecting such animals and/or humans are Ancylostoma, Ascaridia, Ascaris, Aspicularis, Brugia, Bunostomum, Capillaria, Chabertia, Cooperia, Dictyocaulus, Dirofilaria, Dracunculus, Enterobius, Haemonchus, Heterakis, Loa, Necator, Nematodirus, Nematospiroides (Heligomoroides), Nippostrongylus, Oesophagostomum, Onchocerca, Ostertagia, Oxyuris, Parascaris, Strongylus, Strongyloides, Syphacia, Toxascaris, Toxocara, Trichonema, Trichostrongylus, Trichinella, Trichuris, Triodontophorus, Uncinaria and Wuchereria.

Examples of ectoparasites infecting animals and/or humans are arthropod ectoparasites such as biting insects, blowfly, fleas, lice, mites, sucking insects, ticks and other dipterous pests.

Examples of genera of such ectoparasites infecting animals and/or humans are Ambylomma, Boophilus, Chorioptes, Culliphore, Demodex, Damalinia, Dermatobia, Gastrophilus, Haematobia, Haematopinus, Haemophysalis, Hyaloma, Hypoderma, Ixodes, Linognathus, Lucilia, Melophagus, Oestrus, Otobius, Otodectes, Psorergates, Psoroptes, Rhipicephalus, Sarcoptes, Stomoxys and Tabanus.

The compounds according to the invention have been found to be effective both in vitro and in vivo against a range of endoparasites and ectoparasites. The antibiotic activity of compounds of the invention may, for example, be demonstrated by their activity against free living nematodes e.g. *Caenorhabiditis elegans*. In particular, we have found that compounds of the invention are active in vivo against parasitic nematodes such as *Nematospiroides dubius* and *Nippostrongylus braziliensis*.

Compounds of the invention are also of use as antifungals, for example, against strains of Candida sp. such as *Candida albicans* and *Candida glabrata* and against yeast such as Saccharomyces carlsbergensis.

Compounds of the invention are also of use in combating insect, acarine and nematode pests in agriculture, horticulture, forestry, public health and stored products. Pests of soil and plant crops, including cereals (e.g. wheat, barley, maize and rice), cotton, tobacco, vegetables (e.g. soya), fruit (e.g. apples, vines and citrus) as well as root crops (e.g. sugarbeet, potatoes) may usefully be treated. Particular examples of such pests are fruit mites and aphids such as *Aphis fabae, Aulacorthum circumflexum, Myzus persicae, Nephotettix cincticeps, Nilparvata lugens, Panonychus ulmi, Phorodon humuli, Phyllocoptruta oleivora, Tetranychus urticae* and members of the genera Trialeuroides; nematodes such as members of the genera Aphelencoides, Globodera, Heterodera, Meloidogyne and Panagrellus; lepidoptera such as Heliothis, Plutella and Spodoptera; grain weevils such as *Anthonomus grandis* and *Sitophilus granarius*; flour beetles such as *Tribolium castaneum*; flies such as *Musca domestica*; fire ants; leaf miners; *Pear psylla; Thrips tabaci*; cockroaches such as *Blatella germanica* and *Periplaneta americana* and mosquitoes such as *Aedes aegypti*.

According to the invention we therefore provide compounds of formula (I) as defined above, which may be used as antibiotics. In particular, they may be used in the treatment of animals and humans with endoparasitic, ectoparasitic and/or fungal infections and in agriculture, horticulture, or forestry as pesticides to combat insect, acarine and nematode pests. They may also be used generally as pesticides to combat or control pests in other circumstances, e.g. in stores, buildings or other public places or location of the pests. In general the compounds may be applied either to the host (animal or human or plants or vegetation) or a locus thereof or to the pests themselves.

Compounds of the invention may be formulated for administration in any convenient way for use in veterinary or human medicine and the invention therefore includes within its scope pharmaceutical compositions comprising a compound in accordance with the invention adapted for use in veterinary or human medicine. Such compositions may be presented for use in conventional manner with the aid of one or more suitable carriers or excipients. The compositions of the invention include those in a form especially formulated for parenteral (including intramammary administration), oral, rectal, topical, implant, ophthalmic, nasal or genito-urinary use.

The compounds according to the invention may be formulated for use in veterinary or human medicine by injection and may be presented in unit dose form, in ampoules, or other unit-dose containers, or in multidose containers, if necessary with an added preservative. The compositions for injection may be in the form of suspensions, solutions, or emulsions, in oily or aqueous vehicles, and may contain formulatory agents such as suspending, stabilising, solubilising and/or dispersing agents. Alternatively the active ingredient may be in sterile powder form for reconstitution with a suitable vehicle, e.g. sterile, pyrogen-free water, before use. Oily vehicles include polyhydric alcohols and their esters such as glycerol esters, fatty acids, vegetable oils such as arachis oil or cottonseed oil, mineral oils such as liquid paraffin, and ethyl oleate and other similar compounds. Other vehicles such as propylene glycol may also be used.

Compositions for veterinary medicine may also be formulated as intramammary preparations in either long acting or quick-release bases and may be sterile solutions or suspensions in aqueous or oily vehicles optionally containing a thickening or suspending agent such as soft or hard paraffins, beeswax, 12-hydroxy stearin, hydrogenated castor oil, aluminium stearates, or glyceryl monostearate. Conventional non-ionic, cationic or anionic surface active agents may be used alone or in combination in the composition.

The compounds of the invention may also be presented for veterinary or human use in a form suitable for oral administration, for example in the form of solutions, syrups or suspensions, or a dry powder for constitution with water or other suitable vehicle before use, optionally with flavouring and colouring agents. Solid compositions such as tablets, capsules, lozenges, pills, boluses, powder, pastes, granules, bullets or premix preparations may also be used. Solid and liquid compositions for oral use may be prepared according to methods well known in the art. Such compositions may also contain one or more pharmaceutically acceptable carriers and excipients which may be in solid or liquid form. Examples of suitable pharmaceutically acceptable carriers for use in solid dosage forms include binding agents (e.g. pregelatinised maize starch, polyvinylpyrrolidone or hydroxypropyl methylcellulose); fillers (e.g. lactose, micro-crystalline cellulose or calcium phosphate); lubricants (e.g. magnesium stearate, talc or silica); disintegrants (e.g. potato starch or sodium starch glycollate); or wetting agents (e.g. sodium lauryl sulphate). Tablets may be coated by methods well known in the art.

Examples of suitable pharmaceutically acceptable additives for use in liquid dosage forms include suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid); stabilising and solubilising agents may also be includeed.

Pastes for oral administration may be formulated according to methods well known in the art. Examples of suitable pharmaceutically acceptable additives for use in paste formulations include suspending or gelling agents e.g. aluminium distearate or hydrogenated castor oil; dispersing agents e.g. polysorbates, non-aqueous vehicles e.g. arachis oil or oily esters; stabilising and solubilising agents. The compounds of the invention may also be administered in veterinary medicine by incorporation thereof into animals daily solid or liquid dietary intake, e.g. as part of the daily animal feed or drinking water.

The compounds of the invention may also be administered orally in veterinary medicine in the form of a liquid drench such as a solution, suspension or dispersion of the active ingredient together with a pharmaceutically acceptable carrier or excipient.

The compounds of the invention may also, for example, be formulated as suppositories e.g. containing conventional suppository bases for use in veterinary or human medicine or as pessaries e.g. containing conventional pessary bases.

Compounds according to the invention may be formulated for topical administration, for use in veterinary and human medicine, as ointments, creams, lotions, shampoos, powders, pessaries, sprays, dips, aerosols, drops (e.g. eye or nose drops) or pour-ons. Ointments and creams may, for example, be formulated with an aqueous or oily base with the addition of suitable thickening and/or gelling agents. Ointments for administration to the eye may be manufactured in a sterile manner using sterilised components. Pour-ons may, for example, be formulated for veterinary use in oils containing organic solvents, optionally with formulatory agents e.g. stabilising and solubilising agents.

Lotions may be formulated with an aqueous or oily base and will in general also contain one or more emulsifying agents, stabilising agents, dispersing agents, suspending agents, thickening agents, or colouring agents.

Powders may be formed with the aid of any suitable powder base. Drops may be formulated with an aqueous or non aqueous base also comprising one or more dispersing agents, stabilising agents, solubilising agents or suspending agents. They may also contain a preservative.

For topical administration by inhalation the compounds according to the invention may be delivered for use in veterinary or human medicine in the form of an aerosol spray presentation or an insufflator.

The compounds of the invention may be administered in combination with other pharmaceutically active ingredients.

The total daily dosages of compounds of the invention employed in both veterinary and human medicine will suitably be in the range 1–2000 $\mu$g/kg bodyweight, preferably from 50–1000 $\mu$g/kg and these may be given in divided doses, e.g. 1–4 times per day.

The compounds according to the invention may be formulated in any convenient way for horticultural or agricultural use and the invention therefore includes within its scope compositions comprising a compound according to the invention adapted for horticultural or agricultural use. Such formulations include dry or liquid types, for example dusts, including dust bases or concentrates, powders, including soluble or wettable powders, granulates, including microgranules and dispersible granules, pellets, flowables, emulsions such as dilute emulsions or emulsifiable concentrates, dips such as root dips and seed dips, seed dressings, seed pellets, oil concentrates, oil solutions, injections e.g. stem injections, sprays, smokes and mists.

Generally such formulations will include the compound in association with a suitable carrier or diluent. Such carriers may be liquid or solid and designed to aid the application of the compound either by way of dispersing it where it is to be applied or to provide a formulation which can be made by the user into a dispersible preparation. Such formulations are well known in the art and may be prepared by conventional methods such as, for example by blending and/or grinding of the active ingredient(s) together with the carrier or diluent, e.g. solid carrier, solvent or surface active agent.

Suitable solid carriers, for use in the formulations such as dusts, granulates and powders may be selected from for example natural mineral fillers, such as diatomite, talc, kaolinite, montmorillonite prophyllite or attapulgite. Highly dispersed silicic acid or highly dispersed absorbent polymers may, if desired, be included in the composition. Granulated adsorptive carriers which may be used may be porous (such as pumice, ground brick, sepiolite or bentonite) or non-porous (such as calcite or sand). Suitable pregranulated materials which may be used and which may be organic or inorganic include dolomite and ground plant residues.

Suitable solvents for use as carriers or diluents include aromatic hydrocarbons, aliphatic hydrocarbons, alcohols and glycols or ethers thereof, esters, ketones, acid amides, strongly polar solvents, optionally epoxidized vegetable oils and water.

Conventional non-ionic, cationic or anionic surface-active agents, e.g. ethoxylated alkyl phenols and alcohols, alkali metal or alkaline earth metal salts of alkyl benzene sulphonic acids, lignosulphonic acids or sulphosuccinic acids or sulphonates of polymeric phenols which have good emulsifying, dispersing and/or wetting properties may also be used either alone or in combination in the compositions.

Stabilizers, anti-caking agents, anti-foaming agents, viscosity regulators, binders and adhesives, photostabilisers as well as fertilizers, feeding stimulants or other active substances may, if desired, be included in the compositions. The compounds of the invention may also be formulated in admixture with other insecticides, acaricides and nematicides.

In the formulations, the concentration of active material is generally from 0.01 to 99% and more preferably between 0.01% and 40% by weight.

Commercial products are generally provided as concentrated compositions to be diluted to an appropriate concentration, for example from 0.001 to 0.0001% by weight, for use.

The compounds of the present invention may be prepared by a number of processes as described in the following where $R^1$, $R^2$, $R^3$ and $R^4$ are as defined for general formula (I) unless specified otherwise.

Thus, according to one process, compounds of formula (I) may be prepared by reaction of a ketone of formula (II)

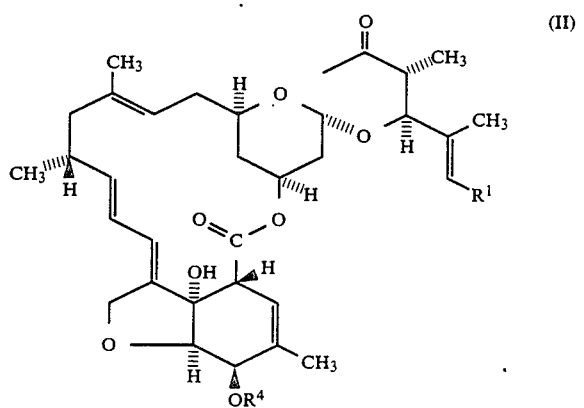

with a reagent serving to introduce the group $R^2$. Suitable reagents include Grignard reagents $R^2MgHal$ (where Hal is a halogen atom, e.g. a chlorine or bromine atom) or organolithium reagents $R^2Li$.

The reaction may be carried out in a suitable solvent such as an ether e.g. diethylether, tetrahydrofuran or a hydrocarbon e.g. n-hexane or a mixture thereof at a temperature of from $-80°$ to $50°$ C., preferably at $-80°$ to $20°$ C. for the reaction with $R^2Li$ and at $0°$ to $50°$ C. for the reaction with $R^2MgHal$.

In a variation of this process a compound of formula (I) in which $R^2$ represents methyl substituted by $CO_2R^5$ (where $R^5$ is as defined above) may be prepared by reacting a ketone of formula (II) with an organolithium reagent $R^5OC{\equiv}CLi$ under the conditions described above followed by hydrolysis using for example a mineral acid such as sulphuric acid in an ether solvent e.g. aqueous tetrahydrofuran.

In another process, compounds of formula (I) may be prepared by interconversion of other compounds of formula (I).

Thus, a compound of formula (I) in which $OR^4$ is a hydroxyl group may be prepared from a corresponding compound of formula (I) in which $OR^4$ is a substituted hydroxyl group by removal of the group $R^4$. The conversion will usually be carried out in the context of removing a protecting group such as referred to above.

Deprotection of the compounds of the invention in which $-OR^4$ represents a protected hydroxyl group can be effected by conventional methods, for example those extensively described in the aforementioned textbooks of McOmie and Greene. Thus, for example, an acyl group such as an acetyl group may be removed by basic hydrolysis, e.g. using sodium or potassium hydroxide or ammonia in an aqueous alcohol such as methanol. An acetal group such as tetrahydropyranyl may be removed for example, using acid hydrolysis (using an acid such as acetic or trifluoroacetic acid or a dilute mineral acid). Silyl groups may be removed using fluoride ions (e.g. from a tetraalkylammonium fluoride such as tetra-n-butylammonium fluoride), hydrogen fluoride in aqueous acetonitrile or an acid such as p-toluene sulphonic acid (e.g. in methanol). Arylmethyl groups may be removed by treatment with a Lewis acid (e.g. boron trifluoride-etherate) in the presence of a thiol (e.g. ethanethiol) in a suitable solvent such as dichloromethane at e.g. room temperature.

In a further interconversion process, a compound of formula (I) in which $-OR^4$ is a hydroxyl group may be converted to a compound of formula (I) in which $-OR^4$ is a substituted hydroxyl group by reaction with a reagent serving to introduce a group $R^4$. The reaction will in general be an acylation, formylation, sulphonylation, etherification, silylation or acetal formation.

Thus, for example, acylation may be effected using an acylating agent such as an acid of formula $R^7COOH$ or a reactive derivative thereof, such as an acid halide (e.g. acid chloride), anhydride or activated ester, or a reactive derivative of a carbonic acid $R^7OCOOH$ or thiocarbonic acid $R^7OCSOH$.

Acylations employing acid halides and anhydrides may if desired be effected in the presence of an acid binding agent such as a tertiary amine (e.g. triethylamine, dimethylaniline or pyridine), inorganic bases (e.g. calcium carbonate or sodium bicarbonate), and oxiranes such as lower 1,2-alkylene oxides (e.g. ethylene oxide or propylene oxide) which bind hydrogen halide liberated in the acylation reaction.

Acylations employing acids are desirably conducted in the presence of a condensing agent, for example a carbodiimide such as N,N'-dicyclohexylcarbodiimide or N-ethyl-N'$\gamma$-dimethylaminopropylcarbodiimide; a carbonyl compound such as carbonyldiimidazole; or an isoxazolium salt such as N-ethyl-5-phenylisoxazolium perchlorate.

An activated ester may conveniently be formed in situ using, for example, 1-hydroxybenzotriazole in the presence of a condensing agent as set out above. Alternatively, the activated ester may be preformed.

The acylation reaction may be effected in aqueous or non-aqueous reaction media, conveniently at a temperature in the range $-20°$ to $+100°$ C., e.g. $-10°$ to $+50°$ C.

Formylation may be effected using an activated derivative of formic acid e.g. N-formyl imidazole or formic acetic anhydride under standard reaction conditions.

Sulphonylation may be effected with a reactive derivative of a sulphonic acid $R^9SO_3H$ such as a sulphonyl halide, for example a chloride $R^9SO_2Cl$. The sulphonylation is preferably effected in the presence of a suitable acid binding agent as described above.

Etherification may be effected using a reagent of formula $R^8Y$ (where $R^8$ is as previously defined and Y represents a leaving group such as chlorine, bromine or iodine atom or a hydrocarbylsulphonyloxy group, such as mesyloxy or tosyloxy, or a haloalkanoyloxy group such as dichloroacetoxy). The reaction may be carried out by formation of a magnesium alkoxide using a Grignard reagent such as a methylmagnesium halide e.g. methylmagnesium iodide or using a trialkylsilylmethylmagnesium halide e.g. trimethylsilylmethylmagnesium chloride followed by treatment with the reagent $R^8Y$.

Alternatively, the reaction may be effected in the presence of a silver salt such as silver oxide, silver perchlorate, silver carbonate or silver salicylate or mixtures thereof, and this system may be particularly appropriate when etherification is carried out using an alkyl halide (e.g. methyl iodide).

Etherification may conveniently be effected in a solvent such as an ether e.g. diethyl ether.

Acetal formation may be carried out by reaction with a cyclic or acyclic vinyl ether. This method is especially useful for production of tetrahydropyranyl ethers, using dihydropyran as reagent, or 1-alkoxyalkyl ethers such as 1-ethoxyalkyl ether, using an alkyl vinyl ether as reagent. The reaction is desirably carried out in the presence of a strong acid catalyst, for example a mineral acid such as sulphuric acid, or an organic sulphonic acid such as p-toluene sulphonic acid, in a non-hydroxylic, substantially water-free solvent.

Silylation may be effected by reaction with a silyl halide (e.g. chloride), advantageously in the presence of a base such as imidazole, triethylamine or pyridine, using a solvent such as dimethylformamide.

The compounds of formula (II) are either known compounds described in UK Patent Specification No. 2176182A or may be prepared from the known compounds using methods analogous to those described therein.

The invention is further illustrated by the following Examples. All temperatures are in °C. The compounds are hereinafter named by reference to the known parent "Factor", Factor A, which is a compound of formula (I) in which $R^1$ is isopropyl, $R^2$ is hydrogen, $R^3$ is hydroxy and $R^4$ is hydrogen. Factor A may be prepared as described in UK Patent Specification No. 2166436A.

EXAMPLE 1

23-Methyl Factor A

A solution of methylmagnesium iodide in diethyl ether (1M, 17 ml) was added to a stirred solution of Factor A 23-ketone (1.00 g, Example 21 in UK No. 2176182A) in diethyl ether (50 ml). The resulting white suspension was stirred at 22° for 30 min. Saturated ammonium chloride (250 ml) was added and the mixture was extracted with diethyl ether ($3 \times 320$ ml). The combined extracts were dried and concentrated to give a yellow foam which was purified by medium pressure chromatography on silica (120 g, Merck Kieselgel 60, 230–400 mesh). Elution with dichloromethane:ethyl acetate (4:1) gave the title compound as a white foam (0.773 g), $[\alpha]_D^{23} + 130°$ (c 0.23, $CH_2Cl_2$); $\lambda_{max}$ (EtOH) 245.5 nm ($\epsilon$ 30150); $\nu_{max}$ ($CHBr_3$). 3490 (OH) and 1708 $cm^{-1}$ (carbonyl); $\delta$ ($CDCl_3$) includes 3.88 (s, 1H), 4.04 (s, 1H) and 1.15 (s, 3H), m/z includes 626, 608, 480, 462, 368, 314, 311, 279, 261, 233 and 151.

EXAMPLE 2

23-Ethyl Factor A

A solution of Factor A 23-ketone (600 mg, Example 21 in UK No. 2176182A) in diethyl ether (30 ml) was treated as in Example 1 but using ethyl magnesium iodide in place of methylmagnesium iodide. The product was isolated as for Example 1 to give a yellow foam which was purified by medium pressure column chromatography on silica (90 g, Merck Kieselgel 60, 230–400 mesh). Elution with dichloromethane:ethyl acetate (5:1) gave the title compound as a white foam (440 mg), $[\alpha]_D^{23} + 129°$ (c 0.17, $CH_2Cl_2$), $\lambda_{max}$ (EtOH) 245.5 nm ($\epsilon$ 29480), $\nu_{max}$ ($CHBr_3$) 3550, 3495 (OH) and 1711 $cm^{-1}$ (carbonyl), $\delta$ ($CDCl_3$) includes 0.85 (t, J=7 Hz, 3H), 3.88 (s, 1H) and 4.02 (s, 1H).

EXAMPLE 3

23-Vinyl Factor A

A solution of Factor A 23-ketone (256 mg, Example 21 in UK No. 2176182A) in diethyl ether (15 ml) was stirred under an atmosphere of nitrogen. A solution of vinylmagnesium bromide in tetrahydrofuran (1.26 ml, 1M) was added and the mixture was stirred at 22° for 2 h. More vinylmagnesium bromide solution (1.26 ml) was added and the mixture was stirred for a further 30 min. Saturated ammonium chloride solution (60 ml) was added and the mixture was extracted with diethyl ether ($3 \times 100$ ml). The extracts were dried and concentrated to give a white foam which was purified by column chromatography on silica (110 g, Merck Kieselgel 60, 230–400 mesh). Elution with dichloromethane:ethyl acetate (4:1) gave a white foam (129 mg). This material was further purified by preparative h.p.l.c. on a column packed with Spherisorb $5\mu$ ODS-2. Elution with 90% acetonitrile in water afforded the title compound as a white foam (67 mg), $[\alpha]_D^{23} + 133°$ (c 0.13, $CH_2Cl_2$), $\lambda_{max}$ (EtOH) 244.5 nm ($\epsilon$ 26640), $\nu_{max}$ ($CHBr_3$) 3490 (OH) and 1710 $cm^{-1}$ (carbonyl), $\delta$ ($CDCl_3$) includes 3.87 (s, 1H), 4.24 (s, 1H), 5.10 (dd, J=10, 2 Hz, 1H), 5.34 (dd, J=17,2 Hz, 1H) and 5.65 (dd, J=17,10 Hz, 1H), m/z includes 638, 620, 526, 508, 492, 380, 314, 291, 273, 245 and 151.

EXAMPLE 4

23-Methyl Factor A and 23-Methyl Factor A 5-acetate

A solution of methylmagnesium iodide in diethyl ether (0.35 ml, 1M) was added to a stirred solution of Factor A 5-acetate 23-ketone (215 mg, Example 18 in UK No. 2176182A) in diethyl ether (10 ml) at 23°. At intervals during 24 h, further quantities of methylmagnesium iodide solution were added (total 1.7 ml, 1M solution). Saturated ammonium chloride solution (50 ml) was added and the mixture was extracted with diethyl ether ($2 \times 100$ ml). The extracts were dried and concentrated to give a crude mixture of products which were purified by medium pressure chromatography on silica (150 g, Merck Kieselgel 60, 230–400 mesh). Elution with dichloromethane:ethyl acetate (9:1) gave a crude product (80 mg). Further elution with ethyl acetate gave 23-methyl Factor A as a white foam (28 mg). The n.m.r. spectrum (in $CDCl_3$) showed that the product was identical to that obtained in Example 1.

The crude product obtained above (80 mg) was further purified by medium pressure chromatography on silica (100 g, Merck Kieselgel 60, 230–400 mesh). Elution with toluene:diethyl ether (4:1) gave a product (44 mg). This was purified by preparative h.p.l.c. on a column packed with Spherisorb 5µ ODS-2. Elution with 75% acetonitrile in water gave 23-methyl Factor A 5-acetate as a white foam (16 mg), $[\alpha]_D^{23}+110°$ (c 0.145, $CH_2Cl_2$), $\nu_{max}$ ($CHBr_3$) 3480 (OH) 1735 and 1710 $cm^{-1}$ (carbonyls), δ ($CDCl_3$ includes 1.15 (s, 3H), 2.18 (s, 3H), 3.80 (s, 1H), 4.05 (s, 1H) and 5.56 (m, 1H); m/z include 668, 650, 608, 590, 538, 480, 462, 368, 314, 311, 279, 261, 251, 233 and 151.

EXAMPLE 5

23-n-Butyl Factor A

A solution of n-butyl lithium in hexane (1.36M, 1.1 ml) was added, with stirring in an atmosphere of nitrogen, to a solution of Factor A 5-acetate 23-ketone (0.501 g, Example 18 in UK No. 2176182A) in ether (20 ml). Further portions of the n-butyl lithium solution (each 1.1 ml) were added after 0.5 h and 1.5 h. The mixture was stirred at 22° for 16 h. Saturated ammonium chloride solution (100 ml) was added and the mixture was extracted with ether (2×200 ml). The combined extracts were dried and concentrated to give an orange foam which was purified by medium pressure chromatography on silica (100 g, Merck Kieselgel 60, 230–400 mesh). Elution with toluene:ether (20:1, 300 ml) removed a non-polar impurity. Subsequent elution with toluene:ether (1:1) gave the title compound as a yellow foam (38 mg), $[\alpha]_D^{23}+90°$ (c, 0.2, $CH_2Cl_2$); $\lambda_{max}$ (EtOH) 245.5 nm (ε 23380); $\nu_{max}$ 3500 (OH) and 1715 $cm^{-1}$ (ester); δ ($CDCl_3$) includes ca. 0.91 (m), 3.88 (s, 1H) and 4.04 (s, 1H); m/z includes 668, 650, 522 353, 321, 303, 275 and 151.

EXAMPLE 6

23-Allyl Factor A

A solution of allylmagnesium chloride in tetrahydrofuran (1.75M, 2.17 ml) was added to a stirred solution of Factor A 5-acetate 23-ketone (0.506 g, Example 18 in UK No. 2176182A) in diethyl ether. Further portions of the allylmagnesium chloride solution (0.87 ml and 1.30 ml) were added after 2 h and 4 h respectively. The mixture was stirred at ca. 23° for 20 h. Saturated ammonium chloride solution (120 ml) was added and the mixture was extracted with ether (2×250 ml). The combined extracts were concentrated and the residue was purified by medium pressure chromatography on silica (110 g, Merck Kieselgel 60, 230–400 mesh). Elution with toluene:ether (2:1, 300 ml) removed an non-polar by-product. Subsequent elution with toluene:ether (1:1) gave the title compound as a white solid (57 mg), $[\alpha]_D^{23}+97°$ (c 0.1, $CH_2Cl_2$); $\lambda_{max}$ (EtOH) 245 nm (ε 28330); δ ($CDCl_3$) includes 4.09 (s, 1H), 5.07 (m 1H), 5.09 (m, 1H) and 5.6–5.9 (m, 3H); m/z includes 652, 634, 506, 305, 287, 277 and 151.

EXAMPLE 7

23-Ethyl Factor A 5-acetate

23-Ethyl Factor A (399.5 mg) was dissolved in pyridine (1.93 ml) and stirred during the addition of acetic anhydride (0.106 ml). The resulting mixture was stirred at 22° for 17 h. A further portion of acetic anhydride (0.035 ml) was added and stirring was continued for a further 24 h. The reaction mixture was poured into 1M-sulphuric acid (62 ml) and extracted with ethyl acetate (1×40 ml, 3×20 ml). The combined extracts were washed with water (2×40 ml), dried and concentrated to give a white foam (400 mg) which was purified by medium-pressure chromatography on silica (80 g, Merck kieselgel 60, 230–400 mesh). Elution with dichloromethane:ethyl acetate (20:1) gave the title compound as a white foam (377 mg), $[\alpha]_D^{23}+128°$ (c 0.30, $CH_2Cl_2$); $\lambda_{max}$ (EtOH) 245.5 nm (ε 29910); $\nu_{max}$ ($CHBr_3$) 3495 (OH), 1734 (acetate) and 1715 $cm^{-1}$ (lactone); δ ($CDCl_3$) includes 0.85 (t, J=7 Hz, 3H), 2.16 (s, 3H), 3.77 (s, 1H), 4.02 (s, 1H), 4.02 (s, 1H) and 5.55 (m, 1H).

The following are examples of formulations according to the invention. The term "Active Ingredient" as used hereinafter means a compound of the invention.

Multidose Parenteral Injection

|  | % w/v | Range |
|---|---|---|
| Active Ingredient | 4.0 | 0.1–7.5% w/v |
| Benzyl alcohol | 2.0 |  |
| Glyceryl triacetate | 30.0 |  |
| Propylene glycol | to 100.0 |  |

Dissolve the active ingredient in the benzyl alcohol and glyceryl triacetate. Add propylene glycol and make up to volume. Sterilise the product by conventional pharmaceutical methods, for example sterile filtration or by heating in an autoclave and package aseptically.

Aerosol Spray

|  | % w/w | Range |
|---|---|---|
| Active Ingredient | 0.1 | 0.01–2.0% w/w |
| Trichloroethane | 29.9 |  |
| Trichlorofluoromethane | 35.0 |  |
| Dichlorodifluoromethane | 35.0 |  |

Mix the Active Ingredient with trichloroethane and fill into the aerosol container. Purge the headspace with the gaseous propellant and crimp the valve into position. Fill the required weight of liquid propellant under pressure through the valve. Fit with actuators and dustcaps.

Tablet

Method of manufacture—wet granulation

|  | mg |
|---|---|
| Active Ingredient | 250.0 |
| Magnesium stearate | 4.5 |
| Maize starch | 22.5 |
| Sodium starch glycolate | 9.0 |
| Sodium lauryl sulphate | 4.5 |
| Microcrystalline cellulose | to tablet core weight of 450 mg |

Add sufficient quantity of a 10% starch paste to the active ingredient to produce a suitable wet mass for granulation. Prepare the granules and dry using a tray or fluid-bed drier. Sift through a seive, add the remaining ingredients and compress into tablets.

If required, film coat the tablet cores using hydroxypropylmethyl cellulose or other similar film-forming material using either an aqueous or non-aqueous solvent system. A plasticizer and suitable colour may be included in the film-coating solution.

Veterinary Tablet for Small/Domestic Animal use

Method of manufacture—dry granulation

|  | mg |
|---|---|
| Active Ingredient | 50.0 |
| Magnesium stearate | 7.5 |
| Microcrystalline cellulose to tablet core weight of | 75.0 |

Blend the active ingredient with the magnesium stearate and microcrystallise cellulose. Compact the blend into slugs. Break down the slugs by passing through a rotary granulator to produce free-flowing granules. Compress into tablets.

The tablet cores can then be film-coated, if desired, as described above.

Veterinary Intrammary Injection

|  | | mg/dose | Range |
|---|---|---|---|
| Active Ingredient |  | 150 mg | 0.05–1.0 g |
| Polysorbate 60 | 3.0% w/w |  |  |
| White Beeswax | 6.0% w/w | to 3 g | to 3 or 15 g |
| Arachis oil | 91.0% w/w |  |  |

Heat the arachis oil, white beeswax and polysorbate 60° to 160° C. with stirring. Maintain at 160° C. for two hours and then cool to room temperature with stirring. Aseptically add the active ingredient to the vehicle and disperse using a high speed mixer. Refine by passing through a colloid mill. Aseptically fill the product into sterile plastic syringes.

Veterinary Oral Drench

|  | % w/v | Range |
|---|---|---|
| Active Ingredient | 0.35 | 0.01–2% w/v |
| Polysorbate 85 | 5.0 |  |
| Benzyl alcohol | 3.0 |  |
| Propylene glycol | 30.0 |  |
| Phosphate buffer | as pH 6.0–6.5 |  |
| Water | to 100.0 |  |

Dissolve the active ingredient in the Polysorbate 85, benzyl alcohol and the propylene glycol. Add a proportion of the water and adjust the pH to 6.0–6.5 with phosphate buffer, if necessary. Make up to final volume with the water. Fill the product into the drench container.

Veterinary Oral Paste

|  | % w/w | Range |
|---|---|---|
| Active Ingredient | 7.5 | 1–30% w/w |
| Saccharin | 25.0 |  |
| Polysorbate 85 | 3.0 |  |
| Aluminium distearate | 5.0 |  |

|  | % w/w | Range |
|---|---|---|
| -continued |  |  |
| Fractionated coconut oil | to 100.0 |  |

Disperse the aluminium distearate in the fractionated coconut oil and polysorbate 85 by heating. Cool to room temperature and disperse the saccharin in the oily vehicle. Dispense the active ingredient in the base. Fill into plastic syringes.

Granules for Veterinary In-Feed Administration

|  | % w/w | Range |
|---|---|---|
| Active Ingredient | 2.5 | 0.05–5% w/w |
| Calcium sulphate, hemi-hydrate | to 100.0 |  |

Blend the Active Ingredient with the calcium sulphate. Prepare the granules using a wet granulation process. Dry using a tray or fluid-bed drier. Fill into the appropriate container.

Emulsifiable Concentrate

| Active ingredient | 50 g |
|---|---|
| Anionic emulsifier (e.g. Phenyl sulphonate CALX) | 40 g |
| Non-ionic emulsifier (e.g. Syperonic NP13) | 60 g |
| Aromatic solvent (e.g. Solvesso 100) | to 1 litre. |

Mix all ingredients, stir until dissolved.

Granules

| (a) | Active ingredient | 50 g |
|---|---|---|
|  | Wood resin | 40 g |
|  | Gypsum granules (20–60 mesh) (e.g. Agsorb 100A) | to 1 kg |
| (b) | Active ingredient | 50 g |
|  | Syperonic NP13 | 40 g |
|  | Gypsum granules (20–60 mesh) | to 1 kg. |

Dissolve all ingredients in a volatile solvent e.g. methylene chloride, add to granules tumbling in mixer. Dry to remove solvent.

We claim:

1. A compound of formula (I)

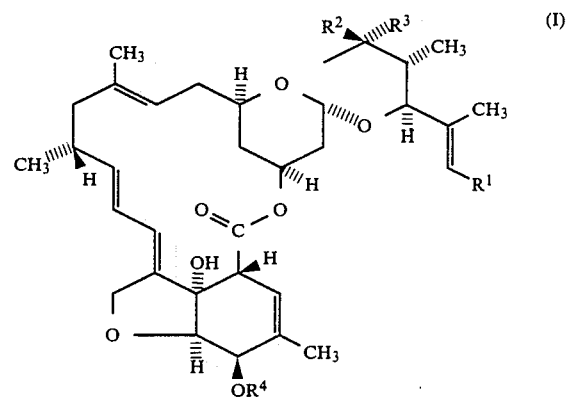

wherein
$R^1$ is a methyl, ethyl or isopropyl group;

$R^2$ is a $C_{1-4}$ alkyl group, optionally substituted by a group $CO_2R^5$ where $R^5$ is a hydrogen atom or a $C_{1-4}$ alkyl group; a $C_{2-6}$ alkenyl group; phenyl or phenyl $C_{1-3}$ alkyl group; $R^3$ is a hydroxy group; and $OR^4$ is a hydroxy or substituted hydroxy group which is a group $-OCOR^7$, $-OCO_2R^7$ or $-OCSOR^7$, where $R^7$ is $C_{1-8}$ alkyl, $C_{1-8}$ alkyl substituted by one or more halogen atoms, $C_{1-4}$ alkoxy, phenoxy or silyloxy substituents, $C_{2-8}$ alkenyl, $C_{2-8}$ alkynyl, $C_{3-12}$ cycloakyl, phenylalkyl in which the alkyl portion has 1-6 carbon atoms, or phenyl; a formyloxy group; a group $-OR^8$ where $R^8$ is as defined above for $R^7$; a group $-OSO_2R^9$, where $R^9$ is a $C_{1-4}$ alkyl or toluyl; a silyloxy group; a tetrahydropyranyloxy group; a group $-OCO(CH_2)_nCO_2R^{10}$ where $R^{10}$ is a hydrogen atom or a group as defined for $R^7$ above and n represents zero, 1 or 2; or a group $OCONR^{11}R^{12}$ where $R^{11}$ and $R^{12}$ each independently represent a hydrogen atom or a $C_{1-4}$ alkyl group.

2. A compound according to claim 1 in which $OR^4$ is a hydroxyl, methoxy, acetoxy or methoxycarbonyloxy group.

3. A compound according to claim 1 in which $R^1$ is an isopropyl group.

4. A compound according to claim 1 in which $R^2$ is a methyl, ethyl, vinyl or allyl group.

5. Compounds according to claim 1 in which $R^1$ is an isopropyl group; $R^2$ is a methyl, ethyl, vinyl or allyl group; $R^3$ is a hydroxyl group; and $-OR^4$ is a hydroxyl, methoxy or acetoxy group.

6. A pharmaceutical composition for use in human or veterinary medicine comprising an anti-parasitic or anti-fungal effective amount of a compound according to claim 1 together with a pharmaceutically acceptable carrier.

7. A pesticidal composition containing an effective amount to combat insect, acarine and nematode pests of a compound according to claim 1 for use in agriculture, horticulture or forestry.

8. A method of combatting insect, acarine or nematode pests which comprises applying an effective amount to combat said pests to the pests or habitat for the pests of a composition according to claim 7.

* * * * *